United States Patent [19]
Wade

[11] Patent Number: 5,334,189
[45] Date of Patent: Aug. 2, 1994

[54] DEVICE FOR CONTROLLED DIFFUSION OF A CHEMICAL SUBSTANCE

[76] Inventor: Stephen E. Wade, P.O. Box 774324, Steamboat Springs, Colo. 80477

[21] Appl. No.: 709,693

[22] Filed: Jun. 3, 1991

[51] Int. Cl.$^5$ ............... A61K 9/22; A61M 35/00; A61C 17/06; A61B 5/00
[52] U.S. Cl. ............... 604/890.1; 604/289; 128/632; 422/68.1; 422/69; 433/80; 433/94; 433/136; 433/138
[58] Field of Search ............ 604/268, 289, 892.1, 604/890.1, 891.1; 128/767, 768, 769, 632, 637; 433/93, 94, 80, 136, 138; 422/68.1, 69, 58

[56] References Cited

U.S. PATENT DOCUMENTS

| | | | |
|---|---|---|---|
| Re. 24,693 | 9/1959 | Thompson | 433/93 |
| 3,029,513 | 4/1962 | Fletcher | 433/94 |
| 3,373,735 | 3/1968 | Gallagher | 128/768 |
| 3,979,274 | 9/1976 | Newman . | |
| 4,175,326 | 11/1979 | Goodson | 433/80 |
| 4,325,695 | 4/1982 | Sundelin et al. | 433/94 |
| 4,340,615 | 7/1982 | Goodwin et al. | 128/768 |
| 4,594,326 | 6/1986 | Wade | 128/768 |
| 4,774,962 | 10/1988 | Hebel et al. . | |
| 4,798,207 | 1/1989 | Wade | 128/768 |
| 4,817,632 | 4/1989 | Schramm . | |

FOREIGN PATENT DOCUMENTS 8806723 9/1988 PCT Int'l Appl. ............ 422/58

OTHER PUBLICATIONS

"Cellulose acetate tubular membrane", Chemical Abstracts, 87:24360.

*Primary Examiner*—David Isabella
*Assistant Examiner*—P. Zuttarelli
*Attorney, Agent, or Firm*—Harold A. Burdick

[57] ABSTRACT

A device and methods of use and manufacture are disclosed for controlled diffusion of chemical substances of interest intraorally. The device includes ported structure formed of material that is substantially impermeable to the substance of interest, an inner wall of which defines a compartment communicating through the ports with the exterior of the device. A dispersed layer is formed in the compartment of material having limited permeability, the layer being formed so that contact is maintained with the inner wall across the ports after formation, the ports and the layer thus providing a region of permeability to diffusion of the chemical substance of interest. In use, either the chemical substance of interest or a composition capable of binding itself to the chemical substance of interest is placed in the compartment and the device is positioned in the mouth of a subject where it may remain for extended periods.

10 Claims, 4 Drawing Sheets

Fig_1

Fig_3

Fig_4

Fig_2

Fig_6

Fig-5

Fig_7

Fig_8

DEVICE FOR CONTROLLED DIFFUSION OF A CHEMICAL SUBSTANCE

FEDERALLY SPONSORED RESEARCH

This invention was made with Government support under a research grant (No. MH42031) awarded by the National Institutes of Health. The Government has certain rights in the invention.

FIELD OF THE INVENTION

This invention relates to devices and methods for diffusion of chemical substances, and, more particularly, relates to devices and methods for controlled diffusion of chemical substances of interest intraorally.

BACKGROUND OF THE INVENTION

Frequently, sampling of biological fluids from a subject, for example to determine the concentration of a substance or substances in the biological fluid for purposes of diagnosis, and/or delivery of drugs to a subject, for example to control delivery rate and/or adequacy of drug level, requires sustained or repeated sampling or delivery over a defined, and often extended, time period.

By way of example, the availability of chemical substances in the body to tissue is often subject to temporal fluctuations, such that a series of samples taken over time from the biological fluid would reveal a distribution of concentration values of the substance. In general, it is the net effect of this temporal distribution of concentration values over some time interval, rather than the value that is observed at any particular moment, that is of interest. One measurement of the net effect of temporal fluctuations in substance concentration over some time interval is the summation of momentary concentration values over that interval, or the "time integral" of concentration. The time integral, divided by the length of the time interval over which it was obtained, results in the average concentration of the substance of interest over that time interval.

The time interval that may be of interest varies according to the context of the measurement, but is frequently on the order of hours. Time integrated measurements on a scale of hours reflect a more enduring state of the organism than measurements representative only of momentary conditions.

Frequently, concentrations of a substance of interest are measured in blood, rather than saliva, since blood is the primary means of transporting most substances within the body. However the concentration of a substance of interest in blood is not always the same as the concentration available to other tissues, the latter typically being of greater interest in diagnostics. This is so because substances must diffuse across cell membranes in order to arrive at other tissues from the blood, and because frequently the substance of interest exists in multiple forms in the blood, not all of which are equally able to cross cell membranes.

In particular, the substance of interest may form associations with other substances (such as proteins) that have much lower ability to permeate cell membranes than has the substance of interest in its free, or unbound, form. In such a case, the concentration of the substance of interest available to tissues other than blood may be much more closely related to the concentration of the free form than to the associated, or bound, forms, or aggregates thereof. Frequently, the bound forms are very much more abundant than the free form.

Moreover, saliva has many advantages as a medium for assessing the concentrations of substances available to tissue in humans. Not only is saliva much more convenient to collect than blood or urine, but levels of many substance of interest in saliva generally reflect the concentrations of the free fractions of those substances in blood plasma. To the degree that saliva concentration of a substance of interest mirrors that of the free fraction of the substance in plasma, the saliva concentration provides more direct information about the availability of the substance to tissue.

There are, however, some significant problems in the interpretation of salivary concentrations of substances. These problems are due to two factors. First, in practice, saliva is often contaminated to some extent with blood or blood plasma, thus including the bound fraction of the substance of interest that is essentially unavailable to tissue. Second, the concentrations of substances in saliva fluctuate over time just as in other body fluids.

Consequently, the interpretation of substance concentrations measured in saliva samples is difficult, since it is generally not known whether there was some degree of blood plasma contamination of saliva, or whether the concentration observed reflected a momentary fluctuation or a longer-enduring state.

It would thus be desirable to provide saliva sampling devices and methods that can be used to obtain a sample of a substance of interest, such that the abundance of the substance of interest in this sample specifically reflects the time integral of the concentration of the free fraction of the substance of interest in saliva (to the exclusion of bound forms) over some known time interval, and that eliminate or minimize measurement inaccuracy caused by blood or blood plasma contamination of saliva.

While devices and/or methods have been heretofore suggested and/or utilized for collecting saliva samples intraorally (see, for example, U.S. Pat. Nos. 4,774,692 and 4,817,632), such devices and methods are not particularly adapted to gathering primarily the substance of interest, rather being directed to gathering saliva samples. Where some filtration of saliva samples has been provided (for example by way of a porous membrane surrounding an osmotically active substance as shown in U.S. Pat. No. 4,817,632), the concentration of a substance of interest derived from analysis of a saliva sample thus collected has no obvious relation to the average concentration of the free fraction of the substance over the interval of use, or even to the concentration of such substance at any identifiable moment within the interval, but instead most closely approximates the concentration present during periods of rapid fluid uptake inherent in such heretofore known devices.

Devices and methods have also been heretofore suggested and/or utilized for the purpose of measuring the concentration of a substance of interest in interstitial fluid, and have therefore been designed to be implantable under the skin of an animal (see U.S. Pat. Nos. 4,798,207 and 4,594,326, by the inventor of the herein disclosed invention). Such devices have of necessity provided means for inserting and withdrawing the binding composition utilized to capture the substance of interest in the device, and required construction utilizing materials compatible with in vivo implantation.

While the device and methods of this invention share many of the general principles discussed in U.S. Pat. No. 4,594,326 (relevant portions of the disclosure of which are incorporated herein by this reference), further improvements to adapt the method therein discussed for use in measuring substances of interest in saliva could be utilized.

In particular, means of accumulating a specific substance of interest intraorally from saliva in such a way that the amount accumulated during some time interval is substantially directly representative of the average concentration of the free fraction of the substance (and thus available to other tissue) in the fluid during that time interval could be utilized. In such a case, it would be desirable that such means not depend upon the net accumulation of saliva fluid, nor be limited by volumetric capacity of a device for such accumulation.

By way of further example (in the case of sustained drug delivery), sustained intraoral delivery of an antibiotic such as tetracycline, for the purpose of treating a periodontal infection or the like, would be desirable. In such a case, therapeutic drug levels could be maintained in the oral cavity over a long period of time. This would be advantageous from the point of view of maintaining adequate drug levels at the site of the infection, without exposing other tissues to such high levels of drug, thereby minimizing undesirable side effects. Devices and methods for such sustained intraoral drug delivery could thus be utilized which regulate the transfer of the drug into saliva.

SUMMARY OF THE INVENTION

This invention provides an improved device, and methods of manufacture and use, for controlled diffusion of a chemical substance of interest. The device is particularly well adapted for use in the mouth of a subject, and includes ported structure made of material that is substantially impermeable, an inwardly facing surface of which defines a compartment for receipt of one of the chemical substance of interest and a composition capable of binding to itself the chemical substance of interest. A dispersed layer is formed in the structure of material characterized by limited permeability so that a region of permeability to diffusion of the chemical substance of interest is formed at the port, or ports, in the structure. Means for securing the device within a subject's mouth is connected with the structure.

The material characterized by limited permeability is dispersed in the compartment so that contact is maintained between such material and the inwardly facing surface adjacent to the port after dispersal, a membrane being formed across the port.

The device can be secured in a patient's mouth, for example between the teeth and the cheek, by anchoring the device to a patient's tooth utilizing a securing line attached to the device. In this manner, the device can be maintained in the mouth for extended periods of time, as would be desirable, for example, where time-integrated measurement of the free fraction of a substance of interest in saliva, or where sustained, regulated, oral delivery of a drug, is desired.

It is therefore an object of this invention to provide an improved device and methods for controlled diffusion of a chemical substance of interest.

It is another object of this invention to provide a device and methods for controlled diffusion of a chemical substance of interest in a subject's mouth.

It is still another object of this invention to provide a device and methods for controlled diffusion of a chemical substance of interest in saliva such that the abundance of the substance of interest collected reflects the time integral of the free fraction of the substance in the saliva.

It is yet another object of this invention to provide a device for controlled diffusion of a substance of interest which includes structure substantially impermeable to the substance of interest, an inwardly facing surface of which defines a compartment, the structure having a port therein from the compartment, and a dispersed layer formed in the structure of material characterized by limited permeability, the layer being formed in the structure so that the layer extends from the inwardly facing surface across the port after formation, the layer thereat providing a region of permeability to diffusion of the substance of interest.

It is still another object of this invention to provide a device for controlled diffusion of a chemical substance of interest between saliva in a subject's mouth and the device, the device including structure having an inwardly facing surface which defines a substantially enclosed compartment and having a first, substantially impermeable, region and a second, selectively permeable, region, the second region including a membrane permeable to diffusion thereacross of the substance of interest positioned coextensively with the inwardly facing surface, and means for securing the structure in the subject's mouth.

It is still another object of this invention to provide a method of making devices for controlled diffusion of a chemical substance of interest including the steps of providing structure substantially impermeable to the substance of interest, the structure having an inwardly facing surface defining a compartment and having a port therein from the compartment, and dispersing a material characterized by limited permeability in the compartment so that contact is maintained between the material and the inwardly facing surface adjacent to the port after dispersal, the port and material providing a region of permeability to diffusion of the substance of interest.

It is yet another object of this invention to provide a method of making devices for controlled diffusion of a chemical substance of interest between saliva in a subject's mouth and the device, the method comprising the steps of molding, of substantially impermeable material, a structure having an inwardly facing surface which defines at least a part of a compartment and having a plurality of ports therein from the compartment, forming, in the structure, a membrane across the ports characterized by permeability to diffusion of the chemical substance of interest, and attaching means for securing the device in the subject's mouth with the structure.

It is still another object of this invention to provide a method for controlled diffusion of a chemical substance of interest between a compartment and saliva in a subject's mouth, the method including the steps of providing a device including structure substantially impermeable to the substance of interest, the structure having an inwardly facing surface defining the compartment and having a port therein, the port having material characterized by limited permeability thereacross, the port and material thereby defining a region of permeability to diffusion of the substance of interest, placing one of the substance of interest and a composition capable of binding to itself the substance of interest in the compartment, and positioning the device in the mouth of a subject.

With these and other objects in view, which will become apparent to one skilled in the art as the description proceeds, this invention resides in the novel construction, combination, arrangement of parts and methods substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 1:
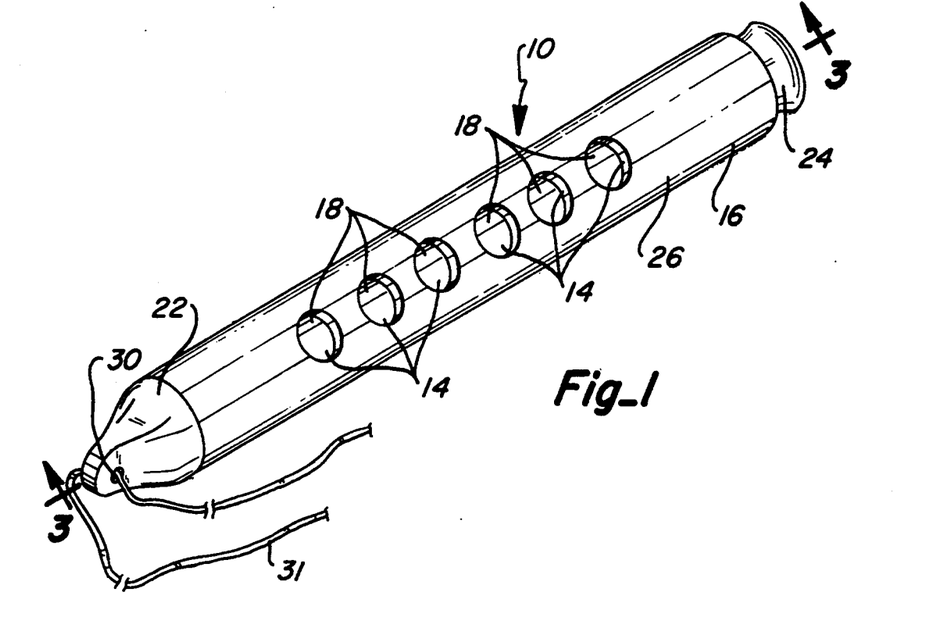
FIG. 1 is a perspective view of a first embodiment of the device of this invention.
Figure 3:
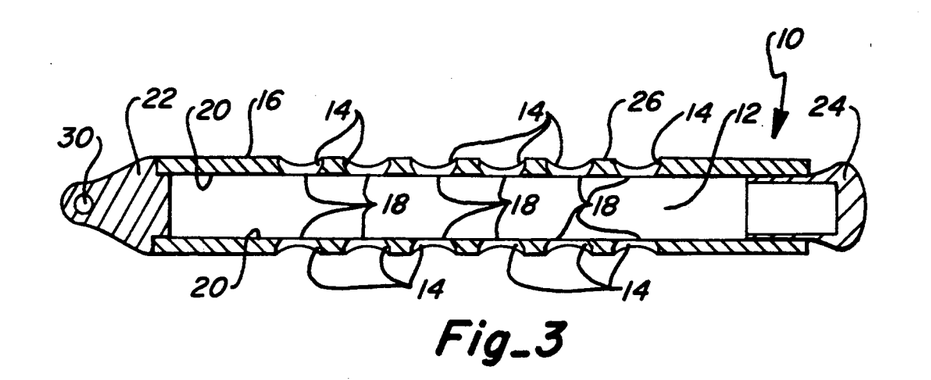
FIG. 3 is a sectional view taken through lines 3—3 of FIG. 1.

A preferred embodiment of device 10 of this invention is illustrated in FIGS. 1 and 3. Interior compartment 12 communicates with the device's immediate environment through multiple diffusion ports 14, preferably arranged in opposing rows on opposite sides of the device. Each diffusion port is formed through shell structure 16 and has a membrane material 18 across the port aperture at a compartment defining the inwardly facing surface 20 of shell 16. Membrane 18 is formed of polymeric material having a limited permeability (i.e., permeable to diffusion of the substance of interest from the immediate environment to compartment 12 or from compartment 12 to the immediate environment) and shell 16 is formed of material which is substantially impermeable, particularly with respect to the substance of interest and other substances found therewith.

Membrane 18, when formed as hereinafter set forth in compartment 12 of shell 16, is a layer of the polymeric material across ports 14 that remains in contact with surface 20 of shell 16. It is felt that the polymeric material in surface contact with surface 20 may, at least in some cases, have properties quite distinct from the properties displayed by diffusion port membrane 18.

Shell 16 includes end closures 22 and 24 and main body 26. Closure 22 typically is made of a similar material as body 26, and is joined to body 26 by, for example when the material is a polymeric plastic, welding through application of heat and pressure to their region of contact. The end result is that closure 22 and body 26 are a substantially unitary structure. Closure 24 may be in the form of a short tube sealed at the distal end, and is of a size so that it is held in intimate and leak-free contact with surface 20 of main body 26 by radial compression of closure 24 upon insertion. It is apparent, of course, that devices may be made with two closures of the same type. Dimensions of the assembled device are approximately 20 to 25 mm overall length, with a 2 to 3 mm outside diameter (1.52 to 2.52 mm inside diameter). Main body 26 without closures is about 15 mm long. The thickness of the tubular wall of main body 26 is approximately 0.24 mm.

Figure 2:
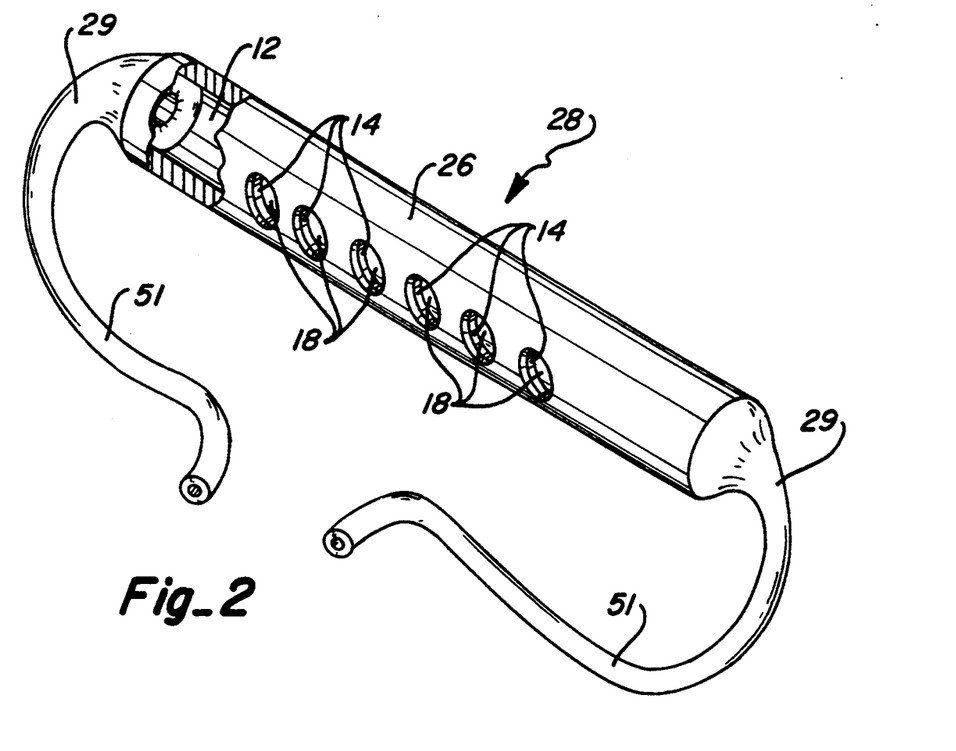
FIG. 2 is a perspective view of a second embodiment of the device of FIG. 1 adapted for use where repeated or constant measurement of the diffused substance of interest is desirable.

In second embodiment 28 of the device shown in FIG. 2, compartment 12 has flow connectors 29 at each end thereof. These connectors are flexible tubes of polymeric material, enabling material in fluid form to be introduced at one end of compartment 12 through a flow connector 29 to consequently displace material from the other end of compartment 12 through the other flow connector 29. The ends of the flow connectors are located at some distant point to facilitate access to the contents of the device without removing the device from the mouth of a subject, as would be useful, for example, in certain research applications where it is desired to make multiple measurements of relatively short duration on a sleeping human subject or for long term administration of a drug to an otherwise incapacitated patient.

Both devices 10 and 28 are preferably provided with means for securing the device in the mouth of a patient. For example, as shown in FIGS. 1 and 3 with respect to device 10, closure 22 may have aperture 30 molded or drilled therethrough for receipt therethrough and attachment (preferably by melting) of securing line 31 (for example, dental floss or other supple line), line 31 being securable to a subject's tooth to secure against loss, swallowing, aspiration, or the like while the device is in the subject's mouth.

Main body 26 is preferably cast in the form of a tube open at each end, and having multiple essentially identical perforations molded into the material to form ports 14. These perforations may be of a variety of shapes. The preferred shape, illustrated in FIG. 4, resembles, in section, a truncated cone with greater diameter port aperture 32 oriented outwardly and lesser diameter port aperture 34 at surface 20 (and being approximately 0.63 mm in diameter). Cylindrical bore portion 36 defines aperture 32, while conical bore portion 38 terminates at aperture 34. The decrease in bore diameter as ports 14 approach surface 20 is valuable in controlling penetration of ports 14 by the membrane casting solution, as described hereinafter.

Figure 4:
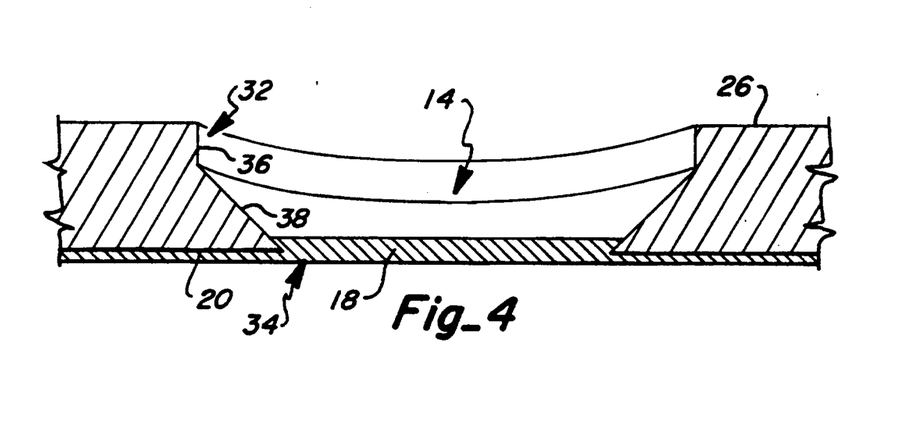
FIG. 4 is a detailed sectional view of a diffusion port structure of the device of FIGS. 1 or 2.

The provision of thin membrane 18 made integral with the more rigid supporting shell structure 16, and in particular the provision of such membranes at surface 20 thereof when that structure has the general configuration of a tube, provides strength and durability, since the otherwise delicate membrane material is supported by intimate contact with the more rigid supporting material and is protected from casual mechanical damage by its position recessed within ports 14. Such strength and durability is particularly advantageous in the application of device 10 or 28 intraorally.

Figure 5:
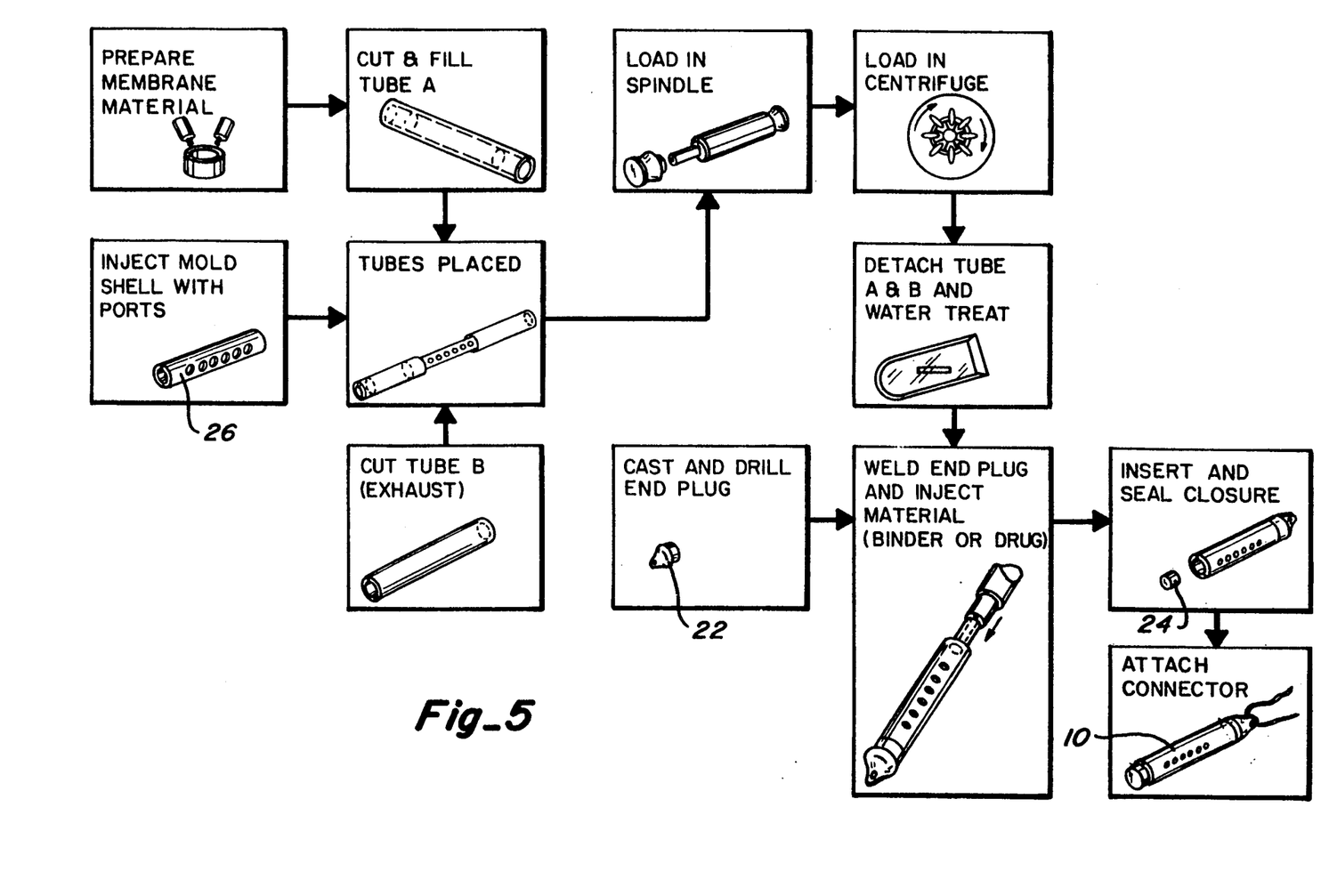
FIG. 5 is a diagrammatic illustration of a method of manufacturing the device of FIGS. 1 or 2 in accord with this invention.

The best method so far devised for making devices 10 or 28 is described with reference to FIG. 5. Main body 26 and closure 22 are produced by injection molding of polycarbonate resin or other suitable material, utilizing known methods. Radioopacity is achieved by adding a radioopaque material (e.g. barium sulfate) to the resin used for injection molding. These parts may be made of other materials such as stainless steel. However, the nature of the contact between membrane 18 and main body 26 of stainless steel is different, as evidenced by the ability to remove tubular membranes intact therefrom, and the inability to do so when using a polymeric main body capable of solvation in the selected solvents.

A solution of the polymer to be used for the membrane is prepared in appropriate organic solvents. Typically a solution of 4 grams cellulose acetate in 14 grams dimethylformamide (DMF) and 7 grams acetone is used (the solvent composition may be varied from about 3:1 to 1:2 acetone to DMF by weight, polymer:solvent proportions being variable in a range from about 1:12.5 to 1:3 by weight). Solution is promoted by stirring and ultrasonication. Other compositions, polymers and/or solvents as are known in the art may also be advantageously used (for example cellulose propionate, cellulose acetate butyrate, or compositions for forming various polycarbonate membranes).

Membrane-modifying materials are added and dissolved. The solution is then further treated by sonication. Typically, for use with binding compositions in device 10, 8 grams citric acid is added to enhance the strength and permeability to solutes of the membrane. Depending on use, this can be varied in a range from no added material to about 2:1 by weight citric acid to cellulose acetate. Other materials, alone or in combination (such as adipic acid with citric acid to accommodate diffusion of larger molecules such as peptides), may be added to vary the resulting properties. It is possible by such means to change the selectivity of membrane 18, for example for passage of solutes of differing molecular weight.

Multiple lengths of polyethylene (PE) tubing are prepared, roughly 30 mm in length and of diameter such that each can make a friction fit over the outside diameter of molded main body 26. A volume of the cellulose acetate solution is loaded into one of the lengths of PE tubing (tube A), the viscosity of the solution generally being of a degree such that the tubing need not be sealed at its end to maintain the solution in the tubing. An assembly is then constructed by attaching the loaded piece of PE tubing (i.e., the dispersing tube) to one end of main body 26, and an empty piece of the tubing (i.e., the receiving, or exhaust, tube B) to the other end of main body 26. Use of materials other than PE, or variations in the means of attaching such tubes, could be utilized.

Multiple resulting assemblies are each loaded in a separate wooden spindle housing having a recess therein for snugly receiving the assembly, the spindles then being loaded in a centrifuge, oriented so that acceleration generated by the centrifuge will act on the cellulose solution to disperse it from the dispersing tube, through main body 26 and into the receiving tube. The centrifuge is operated so as accomplish this movement over a predetermined amount of time. The accelerations provided by the centrifuge may be programmed to vary in order to shorten or prolong the passage of the material through any part of the assemblies. For example, when using an IEC model UV centrifuge with a rotor radius of 150 mm, the controller is initially set to approximately 600 g. The centrifuge approaches this rate setting gradually, usually within about 1 minute. After about 3 minutes the speed controller is advanced in 3 equal steps at 20 second intervals to approximately 900 g., and at about 7 minutes to approximately 1100 g., braking at about 8 minutes.

The pattern of acceleration in the first 4 minutes seems most significant in terms of final results. Overly rapid acceleration (e.g. to 1000 g. at 3 minutes) leads to incomplete membrane formation across apertures 34 of ports 14 due to insufficient deposit of the solution across inwardly facing surface 20, and thus a high frequency of water-leaking devices. Overly slow acceleration (e.g. to only 400 g. at 7 minutes) leads to thick membranes and thick opaque deposits of material along the inside bore of polycarbonate main body 26. The indicated procedure generally gives about a 90% yield of clear, strong, thin, and leak-free membranes.

The assemblies are recovered from the centrifuge and spindles, and main bodies 26 are transferred to water or another suitable solvent, such as methanol, after removal of the lengths of PE tubing. Upon examination after contact with the water, each port 18 in main body 26 will be found to have a thin layer of polymeric material thereat thus together defining regions of selective permeability.

The use of a centrifuge or other appliance to generate a controllable accelerative force that acts upon the volume of solution in the assembly to regulate the flow of this solution at surface 20 across which the solution is being dispersed enables advantageous control over the properties of resulting membrane 18.

For example, the thickness of the membrane deposited may be controlled, in general a greater acceleration producing a thinner membrane from a given casting solution. Similarly, a polymer solution that might otherwise be useless for the purpose of producing membranes because of disadvantageous flow properties may be advantageously used to produce membranes when its flow properties are manipulated by application of appropriate acceleration. In addition, the advantageous properties of the device described here, in particular membrane strength, uniformity and permselectivity, are thought to be at least in part a result of the process herein described.

The product of the process just described is in the form of a tube incorporating diffusion ports, with the tube open at both ends. Closure 22 is installed utilizing an appliance that presses the two parts together in their appropriate orientation and heats the zone of contact so that the parts melt and fuse together. Upon cooling a strong welded bond is made.

Closure 24 is preferably a tube of soft vinyl material, having an outside diameter sufficient to make a snug and leakproof interface with surface 20 of main body 26 upon manual insertion thereinto. This tube can serve as a means for introducing a drug, or the binding composition described hereinbelow, into shell 16 whereupon closure 24 is completed by heating and clamping the distal end of the tube so that shell 16 is entirely closed. The appliance utilized to install closure 22 may be configured to also load the drug or other composition and seal closure 24 in a single step. Securing line 31 is then affixed.

It is to be realized that closures 22 and 24 could be eliminated utilizing a process whereby the ends of main body 26 are collapsed, or pinched closed, and heat sealed, the ends being thereby somewhat enlarged in one dimension.

Of course, where device 28 of FIG. 2 is being constructed, flow connectors 29 are attached (and clamped until ready for use) rather than closures 22 and 24, device 28 typically not being precharged with a drug or binding material.

This method thus establishes membrane 18 at each diffusion port 14 and accomplishes the integral sealing of this membrane component to surface 20 of shell 16 by applying a chemical treatment uniformly, rather than differentially. The application of a chemical treatment uniformly, rather than differentially and selectively as to the regions that are to contain diffusion ports, represents a great advantage in simplicity of construction.

Where polymeric material is utilized to make main body 26 of shell 16, the resulting product is not felt to be merely two juxtaposed layers of material in the impermeable regions, with a single layer of material in the selectively permeable regions at the diffusion ports. Rather, it is now thought that multiple layers of material are not exhibited in the regions of inner wall 20 after dispersal of the membrane material, and that the inner wall in these regions may undergo as a result of treatment some physical or chemical modification, the precise character of which is unknown, but which is thought to result from resolvation (i.e., the polycarbonate material can be etched by the solvents utilized in the described method of making the membrane solution), or some other similar chemical or physical agency in the region of contact.

Where device 10 or 28 is utilized to collect a substance of interest from the saliva of a subject, a binding composition is utilized which determines the specificity and capacity for measurement of the completed device (for example when a binding composition is used as described in U.S. Pat. No. 4,594,326). Since such methods are adaptable to measurement of a great number of substances of interest, the description presented hereinbelow is illustrative of only a few such measurements, others being readily apparent to those skilled in the art. In the examples that follow, the use of an antibody based binding composition is described that can be adapted to measurement of any chemical substance of interest for which a suitable antibody can be found, as is the use of certain whole cells, and of non-antibody, non-protein binding composition for measuring the sex steroids testosterone, progesterone, and estradiol.

The naturally occurring carbohydrate molecule called beta-cyclodextrin has the ability to form non-covalent complexes with certain organic molecules of appropriate size, shape, and polarity. The strength of association of such complexes in the case of the sex steroids testosterone, progesterone, and estradiol was found to be such that a polymer or copolymer incorporating beta-cyclodextrin can serve as a useful binding composition in the practice of the method described in U.S. Pat. No. 4,594,326. Specifically, a beta-cyclodextrin copolymer (obtained from American Maize Co., Hammond, Ind.) is dried and ground to a powder, and the powder is wetted with water to form a slurry that is loaded into device 10 or 28 as described above.

The characteristics of the thus loaded device for uptake of the sex hormones testosterone, progesterone, and estradiol have been found useful in measuring these substances in human saliva over a period of several hours. However, the specificity of the binding composition is such that the related steroid hormone cortisol can not be measured simultaneously. However, neither did cortisol interfere in the measurement of the other steroids.

It is anticipated that other compounds beyond those named above can be measured using beta-cyclodextrin preparations as a binder, and indeed that related cyclodextrins, such as alpha-cyclodextrin and gamma-cyclodextrin, can be used advantageously in the measurement of these and related compounds. This is advantageous in that cyclodextrins are less expensive to prepare and more stable in storage than, for example, the antibodies that are described hereinafter.

It is well known that certain whole cells have the property of responding to hormone exposure with readily-detectable biochemical changes. Such cells may be harvested from among naturally occurring microbes, or can be produced by genetic engineering as described by Pons et al. (BioTechniques 9:450–459, 1990). Use of such cells, or components of such cells, as binding compositions in the present invention may allow the cellular response to hormone exposure to be used as the measure of hormone accumulation. This would advantageously simplify the analytical procedure required in order to measure the amount of hormone accumulated by device 10 or 28.

As a specific example, it is anticipated that cells produced according to the method of Pons et al., and thus having the ability to express the enzyme firefly luciferase only in the presence of the hormone estradiol, and in fact capable of expressing increasing firefly luciferase activity in proportion to increasing degrees of estradiol exposure, could be used as a binding composition for estradiol in the practice of the current invention. After appropriate exposure of device 10 or 28, the amount of accumulated estradiol could be approximately measured by providing appropriate conditions for measuring the activity of the firefly luciferase enzyme induced in the cells by estradiol exposure. This would typically be done by providing an appropriate substrate (e.g. luciferin) and measuring light output, as with a sensitive camera or photometer (as described by Pons et al.).

Generally, the use of an antibody preparation as a binding composition allows the measurement of any substance of interest to which an antibody can be found or produced. This includes the majority of all known hormonal and drug substances. The antibody preparation may be obtained as serum from an animal appropriately immunized, from a culture of tissue, or by other biotechnical means. In the example below, the source of the antibody is serum from an immunized animal.

Where the corticosteroid hormones are to be measured, it is desirable to remove all measurable traces of such compounds from the binding composition. This can be done conveniently in two stages. First, corticosteroids are displaced from binding proteins by addition of a relatively large concentration of a substance that is more weakly bound by those binding proteins. Then the displacing substance is removed by adsorption onto a suitable material.

The displacement step can be accomplished by dialyzing the serum against a buffer containing a large excess of a suitable compound, such as progesterone. For efficiency this can be done using a specialized diafiltration apparatus (such as the Column Effluent Concentrator made by the Amicon Division of W. R. Grace, Danvers, Mass.). The adsorption step can be accomplished by placing the dialyzed serum in contact with a resin such as Amberlite XAD-2 (produced by Rhom & Haas) for many hours. Other preparations may suggest themselves to those skilled in the art.

Upon loading of the binding composition into device 10 and sealing of closure 24, the device is complete and ready for use, some examples of which follow including some in vitro experiments that help to characterize the performance of a corticosteroid-measuring device of this invention, and some preliminary in vivo experiments that illustrate its application in human subjects.

EXAMPLE 1

30 ml of saliva was collected from one subject over the course of about one hour. Blood samples were drawn from the subject using EDTA as the anticoagulant. Plasma was separated immediately. Tritiated cortisol (3H-cortisol) was added to both plasma (0.28 uCi/ml) and saliva (0.014 uCi/ml). The plasma was loaded into a dialysis bag (Spectrapor #4, Spectrum Medical Industries, Los Angeles, Calif.) and dialyzed for 16 hours at 20° C. against the saliva. After this extensive equilibration, whole saliva containing 3H-cortisol was aliquoted to polypropylene vials in 6 replicate volumes of 3 ml. Two of these replicates received 30 ul additions of equilibrated plasma (1% v/v), two received 150 ul equilibrated plasma (5% v/v), and the remaining replicates were uncontaminated with plasma. Devices 10 were incubated (2 per vial) in each preparation, for 3 hours at 20° C. The devices were then recovered and the accumulated radioactivity was determined by liquid scintillation counting. The 3H-cortisol concentration in each vial was likewise determined. The resulting data were examined to determine the effect of blood plasma contamination upon uptake of 3H-cortisol from saliva.

The blood plasma contained 28 times as much 3H-cortisol per unit volume as saliva against which it was extensively dialysed. Addition of equilibrated plasma to saliva at 1% v/v caused an increase of about 35% in total tritiated cortisol (3H-F). Plasma contamination of 5% more than doubled the total 3H-cortisol content. However, as shown in Table 1, performance of the devices was completely unaffected by blood plasma contamination of saliva.

TABLE 1

| Degree of plasma contamination | 3H-F activity nCi/ml | 3H-F uptake nCi |
| --- | --- | --- |
| 0% | 13.6 | 0.834 (0.082) |
| 1% | 18.4 | 0.733 (0.039) |
| 5% | 31.8 | 0.728 (0.027) |

Lack of effect of blood plasma contamination of saliva upon device uptake of tritiated cortisol (3H-F). The distribution of 3H-F between plasma and saliva was equilibrated before the experiment began (see text). The uptake of 3H-F is cumulative over a period of 3 hours at 20° C. (mean and standard error for 4 devices).

EXAMPLE 2

In order to test the capacity of the devices of this invention to accurately integrate extreme changes in hormone concentration, we measured uptake performance of device 10 under three conditions: 1) low, constant cortisol level, 2) high, constant cortisol level, and 3) a single brief pulse of high cortisol concentration against a background of low cortisol concentration.

A buffer containing cortisol with a trace amount of 3H-cortisol at constant specific activity was prepared, containing either 2.8 nmol/L or 28 nmol/L of total cortisol (F). These concentrations correspond to saliva cortisol concentrations observed under low baseline conditions and following pharmacological stimulation, respectively. Devices 10 were incubated under either constant conditions (2 hours in one buffer), or with a transition from low to high cortisol after 1 hour, with a return to the low cortisol environment after 30 min. The transitions were substantially instantaneous. The average cortisol concentration experienced by devices in the "pulse" condition was 9.0 nmol/L. Data were analyzed by plotting cortisol uptake as a function of average cortisol concentration, and examining the colinearity of uptake under the constant and pulsed conditions.

Figure 7:
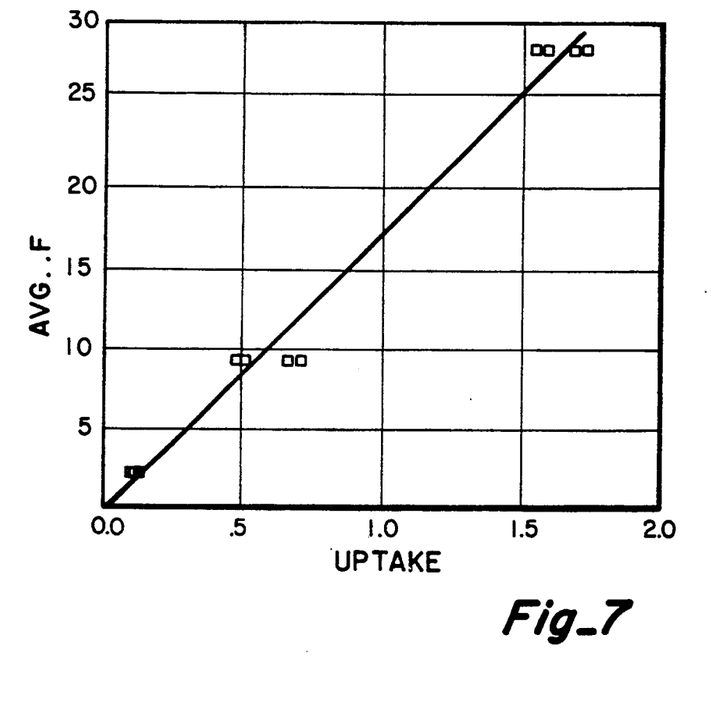
FIG. 7 is a chart illustrating uptake of a chemical substance of interest present in saliva utilizing the device of FIG. 1.

The devices responded accurately in representing the average hormone availability produced by a single brief and extreme pulse of cortisol in the environment. FIG. 7 shows that the data from the pulse condition are superimposable upon the response function determined by performance under the two constant conditions ($r = 0.995$). In FIG. 7, cortisol uptake is expressed in picomoles. Each point represents the response of a single device 10.

EXAMPLE 3

Five healthy normal subjects (two female) were recruited (after advisement and informed consent) for a three-day study of corticosteroid variation between the morning and afternoon of a typical work day.

Figure 6:
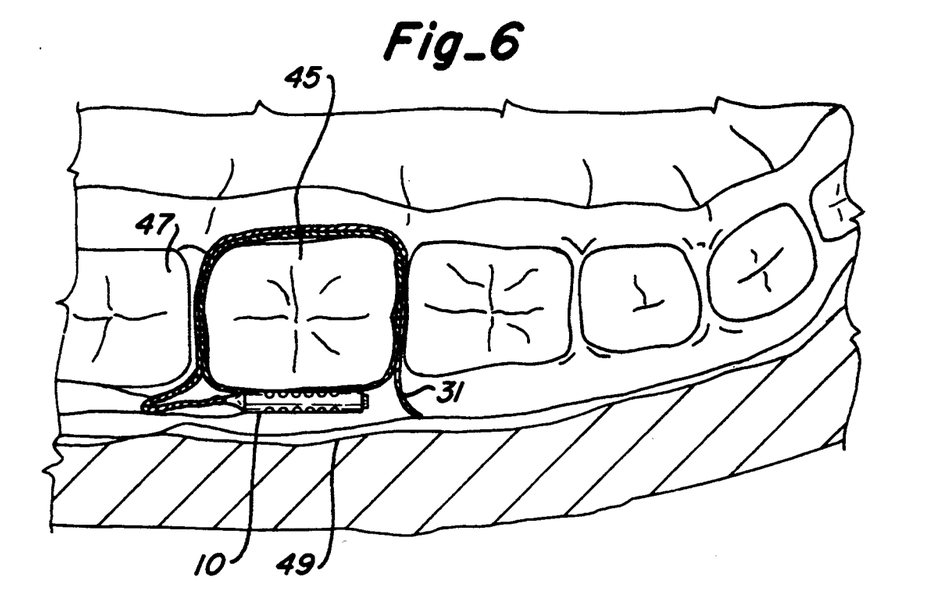
FIG. 6 is an illustration showing use of the device of FIG. 1 intraorally in accord with this invention.

Subjects were issued a package of 12 of the device 10 and were shown how to position and secure each device by wrapping dental floss securing line 31 around tooth 45 as illustrated in FIG. 6. In practice, the subject grasps dental floss securing line 31 attached to device 10 with the thumb and a finger of each hand, one hand near its free end, the other hand about 2 cm from its attachment to device 10. Line 31 is then passed between teeth 45 and 47 at the side of the mouth, much as when floss is used for the purpose of cleaning between teeth, in such a way that device 10 is outside the teeth and adjacent to cheek 49. The free end of line 31 is then passed again in the space between teeth at another site, either toward the front or toward the back of the mouth from the first site. The distance between device 10 and the teeth is regulated to 2 to 3 cm by pulling on the free end of the floss. Finally both passages are repeated, with the result that the floss is wrapped entirely around tooth 47 approximately one and a half times. The excess free floss is then preferably removed with scissors. The choice of which tooth or teeth to use for anchoring, and the exact length of floss to be maintained between the teeth and device 10, is left to the discretion of the subject.

Devices are easily removed after use by grasping line 31 near its attachment to the device and pulling smoothly. Use of device 10 without line 31 is of course possible, but is usually not preferred because of the potential for loss of the device.

Subjects were instructed to install 2 devices 10 (one on each side of the mouth) for two hours sometime during the interval between 0700 and 1100 hours, recording the exact times of installation and removal. Similar measurements were made during the interval between 1300 and 1700 hours. Upon removing the devices, subjects rinsed them in tap water and placed them (pairs together) in screw-capped vials containing methanol. Subjects accumulated 6 sample vials and returned them for analysis after the third consecutive day of sampling. The methanolic extracts of devices 10 were differentially analyzed for corticosteroids by an ultrasensitive HPLC method, which involves forming fluorescent esters of the steroids by reaction at the 21- hydroxy position with anthroyl nitrile. The average saliva concentration (X) corresponding to the reported duration of use (D) and the measured steroid content (C) was calculated using an uptake constant (k) of 0.035 ml h-1 (i.e. $X=(C/D)/k$). The variation of integrated saliva corticosteroid concentration from morning to afternoon, and differences among subjects, were studied by analysis of variance (ANOVA).

Figure 8:
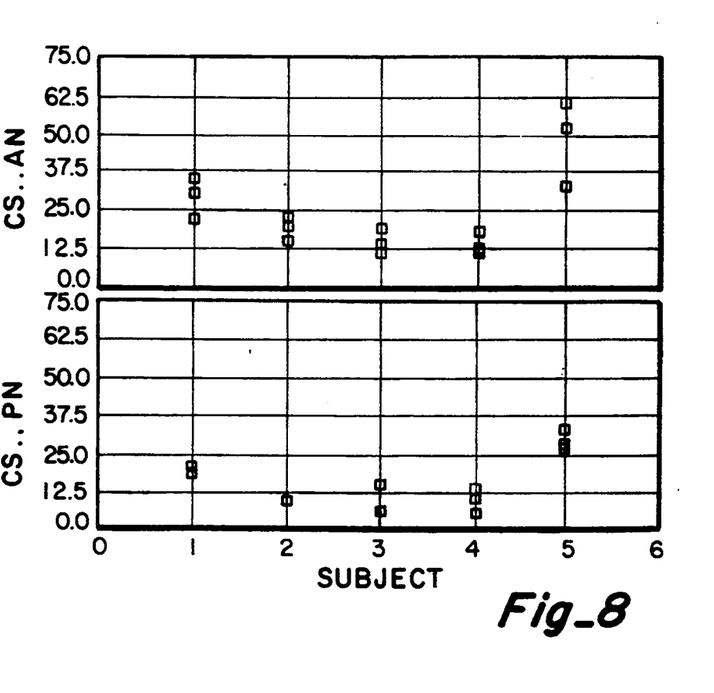
FIG. 8 is a chart illustrating measured concentrations of a chemical substance of interest present in saliva and collected utilizing the device of FIG. 1.

All five subjects completed the protocol, and none reported any discomfort in using devices 10 as instructed. Of the 30 potential observations, 2 from 1 subject and 1 from another subject were lost due to negligent timing. All the missing observations were in the afternoon time period. FIG. 8 represents saliva corticosteroid (cortisol+cortisone) concentrations (nmol/L) measured in the human subjects over 3 days. The upper panel shows morning (0700–1100 hours) values, while the lower panel shows afternoon (1300–1700 hours) values (a significant drop in corticosteroid concentrations from morning to afternoon ($F(1,17)=13.35$, $p<0.002$) being notable). Each point represents a single measurement based on a 2 hour integration.

When device 28 is used, for example when it is desirable to make multiple sequential measurements of saliva concentrations of a substance, or when long term drug delivery is desired, without requiring the subject to repetitively install and remove devices 10, tubing 51 of flow connectors 29 are passed from the corner of the subject's mouth and secured to the cheek with adhesive tape, and further extended and taped to the back of the subject's neck. The tubing is further extended from the subject to the bed in which the subject is confined, finally terminating at a convenient distance so that the ends of the tubing can be accessed by research or medical personnel. Thus, successive measurements can be started and stopped respectively by introducing and removing an appropriate binding composition to device 28 through the attached tubes, or long term drug delivery can be accomplished.

Where the devices of this invention are used in providing sustained delivery of drugs within the oral cavity, for example of antibiotics or the like, compartment 12 of device 10 or 28 would be filled not with a binding composition, but with a drug composition. Diffusion of the drug from compartment 12 of the device into the saliva would follow the same diffusion laws already described, the precisely defined and limited diffusion pathway provided through membranes 18 and ports 14 regulating the rate of transfer of the drug composition to the patient.

As may be appreciated from the foregoing, improved devices and methods for controlled diffusion of chemical substances of interest are provided, the device and methods being particularly well adapted to diffusion of the chemical substances of interest in a subject's mouth.

What is claimed is:

1. A device for controlled diffusion of a chemical substance of interest between a body fluid and said device, said device comprising:
    a structure impermeable to the substance of interest, an inwardly facing surface of which surrounds and in part defines a compartment, said structure having a port defined therein; and
    a diffusion layer formed in said structure characterized by selective permeability to the substance of interest while being substantially impermeable to other substances and the substance of interest bound to any of said other substances, said layer comprising at the time of formation in said compartment a dispersed solution coating substantially all of said inwardly facing surface of said structure thereby establishing said layer in adherence with said inwardly facing surface and across said port.

2. The device of claim 1 wherein said structure includes removable closure means for allowing access to said compartment.

3. The device of claim 1 wherein said device is about 25 mm long and 3 mm in diameter.

4. The device of claim 1 further comprising one of a composition capable of binding to itself the substance of interest and said substance of interest in said compartment.

5. The device of claim 1 wherein said structure includes a main body having said inwardly facing surface and said port thereat, and at least a first flow connector connected with said main body to allow flow of matter to said compartment from a remote location.

6. The device of claim 5 wherein said structure includes a second flow connector connected with said main body to allow flow of matter from said compartment.

7. The device of claim 1 wherein said structure includes a plurality of ports, said layer extending across all of said ports after formation.

8. The device of claim 7 wherein said body fluid is saliva in a subject's mouth and
    wherein said structure is configured for placement in the subject's mouth and has an outer surface, each of said ports having first and second spaced apertures, said first apertures located at said inwardly facing surface and said second apertures being located at said outer surface and being larger than said first apertures.

9. The device of claim 8 further comprising supple securing means connected with said structure for securing said structure entirely in the subject's mouth, said supple securing means having sufficient length to secure said structure to a subject's tooth while leaving a length thereof between said structure and the tooth.

10. The device of claim 8 wherein the substance of interest is present in bound and free fractions in the saliva, and wherein said diffusion layer is characterized by permeability to diffusion of the free fraction and not the bound fraction of the substance of interest

* * * * *